United States Patent
Dominianni

(12)
(10) Patent No.: US 6,617,342 B1
(45) Date of Patent: Sep. 9, 2003

(54) HYPOGLYCEMIC SULFONYL PYRAZOLONES AND PYRAZOLINES

(75) Inventor: Samuel James Dominianni, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/069,029

(22) PCT Filed: Aug. 16, 2000

(86) PCT No.: PCT/US00/20778

§ 371 (c)(1),
(2), (4) Date: Apr. 16, 2002

(87) PCT Pub. No.: WO01/16111

PCT Pub. Date: Mar. 8, 2001

Related U.S. Application Data

(60) Provisional application No. 60/151,166, filed on Aug. 27, 1999.

(51) Int. Cl.⁷ .................... A61K 41/422; C07D 413/02
(52) U.S. Cl. ................... 514/374; 514/404; 514/406; 514/407; 548/235; 548/371.4; 548/377.1; 548/379.1
(58) Field of Search ............ 548/379.1, 371.4, 548/377.1, 235; 514/374, 404, 406, 407

(56) References Cited

U.S. PATENT DOCUMENTS

| | | |
|---|---|---|
| 5,036,079 A | 7/1991 | Clark et al. |
| 5,183,825 A | 2/1993 | Kees |
| 5,306,726 A | 4/1994 | Hulin |
| 5,480,891 A | 1/1996 | Yamasaki et al. |

OTHER PUBLICATIONS

Dick et al, Pharmazie (1971), 26(7), 394–6 (CAS Abstract).*

Lespagnol et al, Bull. Soc. Chim. Biol. 1961, 43, 789–99 (CAS Abstract).*

Kees KL, Caggiano TJ, Steiner KE, et al. Studies on new acidic azoles as glucose–lowering agents in obese, diabetic db/db mice. J Med Chem 1993;38:617–28.*

Kees, Kenneth L., et al., "Studies on New Acidic Azoles as Glucose–Lowering Agents in Obese, Diabetic db/db Mice," *J. Med. Chem.*, vol. 38, No. 4, pp. 617–628 (1995).

Yusuke Sato, et al., "Possibility of ideal blood glucose control by a new oral hypoglycemic agent, N–[(trans–4–isopropylcyclohexyl)–carbonyl]–D–phenylalanine (A–4166), and its stimulatory effect on insulin secretion in animals," *Diabetes Research and Clinical Practice*, 12, pp. 53–60 (1991).

* cited by examiner

*Primary Examiner*—Joseph K. McKane
*Assistant Examiner*—Kamal Saeed
(74) *Attorney, Agent, or Firm*—Francis O. Ginah

(57) ABSTRACT

This invention provides compounds and their pharmaceutically acceptable salts, pharmaceutical formulation of said compounds and methods for treating hyperglycemia associated with non-insulin dependant diabetes and for treating hyperlipidemia.

5 Claims, No Drawings

HYPOGLYCEMIC SULFONYL PYRAZOLONES AND PYRAZOLINES

This application claims benefit of No. 60/151,166 filed Aug. 27, 1999.

FIELD OF THE INVENTION

This invention relates to the treatment and control of hyperglycemia, such as occurs in non-insulin-dependent diabetes mellitus (NIDDM). This invention also relates to treatment and control of hyperlipidemia.

BACKGROUND OF THE INVENTION

The disease, diabetes mellitus, is recognized in two forms. Type I diabetes requires exogenous insulin for control of the disease because it appears that endogenous production of insulin by the Isles of Langerhans in the pancreas is extremely poor or non-existent. Type I diabetes is often referred to as insulin-dependent diabetes mellitus (IDDM). Type II, non-insulin-dependent diabetes mellitus (NIDDM), is characterized by defects of insulin sensitivity in peripheral tissues such as adipose tissue and muscle, as described by J. E. Gerich in *New Engl. J. Med.*, 321, 1231–1245 (1989).

Hyperlipidemia is often observed in diabetics (*Diabetes Care*, 18, Supplement 1, 86–93, 1995). The combination of hyperlipidemia and hyperglycemia greatly increases the risk of cardiovascular diseases in diabetics. Successful treatment of hyperlipidemia and hyperglycemia in diabetics is needed urgently.

Blank reviewed hypoglycemic agents (*Burger's Medicinal Chemistry*, 4th Ed., Part II, John Wiley and Sons, N.Y., 1979, 1057–1080). Newer hypoglycemic agents were reviewed by Hulin in *Progress in Medicinal Chemistry*, 31, ed. G. P. Ellis and D. K. Luscombe, Elsevier Publishing Co., 1993.

Currently, partial control of NIDDM is achieved by a diet and exercise regimen, by administration of exogenous insulin, by administration of hypoglycemic agents, (e.g. the sulfonylureas), or by some combination of these protocols. Sulfonylureas, such as chloropropamide, acetohexamide and tolbutamide, are useful orally-effective hypoglycemic agents achieving success in the control of NIDDM in a number of patients. However, drugs currently available for the control of the hyperglycemia associated with type II diabetes mellitus (NIDDM) possess significant liabilities or limitations of efficacy. (Ellingboe, et al., *J. Med. Chem.* 36:2485–2493, 1993). Considerable effort has been expended toward developing novel, orally-administered antihyperglycemic drugs. A preferred therapeutic approach for treating NIDDM incorporates drugs that counteract insulin resistance rather than those that stimulate endogenous insulin secretion. (J. R. Colca and D. R. Morton, *New Antidiabetic Drugs*, ed. C. J. Bailey and P. R. Flatt, Smith-Gordon and Company, Ltd., London, Chapter 24, 1990). Drugs that treat insulin resistance are called insulin sensitivity enhancers.

Sato, Y, et al. (*Diabetes Research and Clinical Practice*, 12:53–60, 1991) described the hypoglycemic effect of D-phenylalanine derivatives. In normal dogs, the hypoglycemic activity of the compound was greater than that of tolbutamide but less than that of glibenclamide. The compounds exerted a rapid hypoglycemic effect and improved glucose tolerance in genetically diabetic KK mice and in streptozotocin-treated rats. Yamasaki, et al. disclosed a group of 2-quinolone derivatives showing antidiabetic activity in NIDDM (WO 92/21342).

Some known hypoglycemic compounds also reduce serum cholesterol or triglyceride levels. (Clark, et al., U.S. Pat. No. 5,036,079). The combination of these biological activities in one compound is particularly advantageous because diabetics are highly susceptible to hyperlipidemia. Hulin, in U.S. Pat. No. 5,306,726, claimed phenylpropionic acid derivatives and disclosed compounds that had hypoglycemic and hypocholesterolemic activity useful for the treatment of diabetes and atherosclerosis. Miyata, et al. found a class of phosphonic diester derivatives useful for treating diabetes and hyperlipidemia (WO 93/23409). Hypolipidemic amino acid derivatives were disclosed in JA-028189. Highly substituted aryl ethers of tyrosine were reported to have hypocholesterolemic activity (*J. Med. Chem.*, 38:695–707, 1995). No aklyl ethers of tyrosine were disclosed.

Pyrazole compounds have been shown to have hypoglycemic effect. For example, U.S. Pat. No. 5,183,825 issued Feb. 2, 1993 disclosed the use of 4-Arylmethyl-5-alkyl-3H-pyrazol-3-ones as hyperlipidermia.

SUMMARY OF THE INVENTION

The present invention provides novel pyrazolones and pyrazolines useful in the treatment of hyperglycemia and/or hyperglycemia.

The present invention is also a method of use of novel pyrazolones and/or pyrazolines in the treatment of hyperlipidemia and/or hyperglycemia.

The present invention also provides a pharmaceutical composition containing a pyrazolone and/or pyrazoline compound of the invention useful for the treatment of non-insulin dependent diabetes mellitus (NIDDM).

The present invention provides novel compounds having utility as hypoglycemic and hypolipidemic agents of formula I;

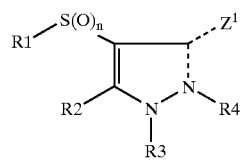

wherein:

$R^1$, $R^2$, $R^3$, and $R^4$ are independently alkyl, aryl aralkyl, heteroaryl, heteroalkyl fragments of 1–20 atoms (including, but not limited to, carbon, hydrogen, oxygen, nitrogen, sulfur, phosphorus, halogen) with or without substituents; $Z^1$ is variously hydrogen, oxygen, sulfur, nitrogen; The dashed bonds are variously single or double; n is an integer from zero to 2.

DEFINITIONS

The terms used to describe the instant invention have the following meanings herein.

A "mammal" is an individual animal that is a member of the taxonomic class mammalia. The class mammalia includes humans, monkeys, chimpanzees, gorillas, cattle, swine, horses, sheep, dogs, cats, mice, and rats.

"$C_{1-4}$ alkyl" refers to a straight or branched alkyl radicals having 1 to 4 carbon atoms, for example, methyl, ethyl, n-propyl, isopropyl, n-butyl, sec-butyl, or t-butyl.

"$C_{1-4}$ alkoxy" refers to a straight or branched chain alkyl radicals attached to oxygen having 1 to 4 carbon atoms, for example, methoxy, ethoxy, n-propoxy, isopropoxy, or t-butoxy, and the like.

The terms "active ingredient" and "active compound" as used herein are synonymous and refer to a compound(s) of the present invention as represented by formula I or its pharmaceutically acceptable salts or prodrug individually contained or combined with other compound(s) of formula I in a formulation of the invention.

The term "aralkyl" refers to an aryl($C_1$–$C_6$-alkyl) group.

The term "aryl" refers to a substituted or unsubstituted aromatic or heteroaromatic radical (wherein the terms "aromatic group" and "heteroaromatic group" refer to common aromatic rings having 4n+2 pi electrons in a monocyclic or bicyclic conjugated system) selected from the group consisting of 2-furyl, 3-furyl, 2-thienyl 3-thienyl, 1-pyrrolyl, 2-pyrrolyl, 3-pyrrolyl, phenyl, 2-pyridyl, 3-pyridyl, 4-pyridyl, 1-naphthyl, 2-naphthyl, 2-benzofuryl, 3-benzofuryl, 4-benzofuryl, 5-benzofuryl, 6-benzofuryl, 7-benzofuryl, 2-benzothieny, 3-benzothienyl, 4-benzothienyl, 5-benzothienyl, 6-benzothienyl, 7-benzothienyl, 1-indolyl, 2-indolyl, 3-indolyl, 4-indolyl, 5-indolyl, 6-indolyl and 7-indolyl. Aryl groups may be optionally substituted at one or two carbon atoms of the aryl group, and may be with $C_{1-4}$ alkyl, $C_{1-4}$ alkoxy, halogen, —$NO_2$, —CN, —COOH, —$CONH_2$, —$SO_3H$, —$SO_2NH_2$ or trifluoromethyl. Examples of substituted aryl groups are 4-methyl-3-furyl, 3,4-dimethyl-2-thienyl, 2,4-dimethyl-3-thienyl, 3-ethoxy-4-methyl-2-benzofuryl, 2-cyano-3-benzofuryl, 4-trifluoromethyl-2-benzothienyl, 2-chloro-3-benzothienyl, 3,4-dichloro-2-pyridyl, 2-bromo-3-pyridyl, 2-fluoro-4-pyridyl, 4-fluoro-2-furyl, 2-carboxyphenyl, 4-carboxamidophenyl, 3-trifluoromethylphenyl, 2-bromo-1-naphthyl, 2,3-dimethyl-1-naphthyl, 3-carboxy-2-naphthyl, 5-carboxy-8-chloro-1-naphthyl, 3-ethyl-2-furyl, 8-fluoro-2-naphthyl, 5-trifluoromethyl-2-naphthyl, 6-ethoxy-2-naphthyl, 6,7-dimethoxy-2-naphthyl, 3-carboxy-2-naphthyl, and the like.

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl, n-pentyl, and n-hexyl.

The term, "alkenyl" employed alone or in combination with other terms means a straight chain or branched monovalent hydrocarbon group having the stated number range of carbon atoms, and typified by groups such as vinyl, propenyl, crotonyl, isopentenyl, and various butenyl isomers.

The term, "hydrocarbyl" means an organic group containing only carbon and hydrogen.

The term, "halo" means fluoro, chloro, bromo, or iodo.

The term, "heterocyclic radical", refers to radicals derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyrrolyl, furanyl, thiophenyl, pyrazolyl, imidazolyl, triazolyl, isoxazolyl, oxazolyl, thiazolyl, thiadiazolyl, indolyl, carbazolyl, norharmanyl, azaindolyl, benzofuranyl, dibenzofuranyl, thianaphtheneyl, dibenzothiophenyl, indazolyl, imidazo[1.2-a]pyridinyl, benzotriazolyl, anthranilyl, 1,2-benzoxazolyl, benzoxazolyl, benzothiazolyl, purinyl, pirydinyl, dipyridylyl, pyrimidinyl, pyrazinyl, 1,3,5-triazinyl, quinolinyl, phthalazinyl, quinazolinyl, and quinoxalinyl.

The terms "alkylheterocyclic" and "arylheterocyclic" refer to radicals formed respectively by the bonding of a substituted or unsubstituted alkyl radical or aryl radical to a heterocyclic radical such that a news radical is generated with the reactive terminus at the alkyl or aryl group respectively.

The term "amino protecting group" as used herein refers to substituents of the amino group commonly employed to block or protect the amino functionality while reaction(s) are carried out at other functional groups of the compound. Examples of such amino-protecting groups include the formyl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcylcopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluorenylmethoxycarbonyl ("FMOC"), 2-(trimethylsilyl)ethoxycarbonyl, allyloxycarbonyl, 1-(trimethylsilylmethyl)prop-1-en-3-yloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl, and the like; the benzoylmethylsulfonyl, the 2-(nitro)phenylsulfenyl group, the diphenylphosphine oxide group and like amino protecting groups. The species of amino protecting group employed is not critical so long as the derivatized amino group is stable to the conditions of subsequent reaction(s) on other positions of the molecule and can be removed at the appropriate point without disrupting the remainder of the molecule. Similar amino protecting groups used in the cephalosporin, penicillin, and peptide arts are also embraced by the above terms. Further examples of groups referred to by the above terms are described by J. S. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7 and T. W. Greene, "Protective Groups in Organic Synthesis", 2nd Ed., John Wiley and Sons, New York, N.Y., 1991. The related term "protected amino" defines an amino group substituted with an amino protecting group discussed above.

The term "carboxy protecting group" as used herein refers to one of the ester derivatives of the carboxylic acid group commonly employed to block or protect the carboxylic acid group while reactions are carried out on other functional groups of the compound. Examples of such carboxylic acid protecting groups include benzyl, 4-nitrobenzyl, 4-methoxybenzyl, 3,4-dimethoxybenzyl, 2,4-dimethoxybenzyl, 2,4,6-trimethoxybenzyl, pentamethylbenzyl, 3,4-methylenediozybenzyl, benzyhydryl, 4,4'-dimethoxybenzhydryl, 2,2,4,4'-tetramethoxybenzhydryl, t-butyl, isobutyl, n-butyl, propyl, isopropyl, ethyl, methyl, t-amyl, trityl, 4-methoxytrityl, 4,4'-dimethoxytrityl, 4,4',4"-trimethoxytrityl, trimethylsilyl, t-butyldimethylsilyl, phenyacyl, 2,2,2-trichloroethyl, p-toluenesulfonylethyl, 4-nitrobenzylsulfonylethyl, allyl, cinnamyl, or 1-(trimethylsilylmethyl)prop-1-en-3-yl, and like moieties. The species of carboxy-protecting group employed is not critical so long as the derivatized carboxylic acid is stable to the conditions of subsequent reaction(s) on other positions of the molecule and can be removed at the appropriate point without disrupting the remainder of the molecule. Carboxy protecting groups similar to those used in the cephalosporin, penicillin, and peptide arts can also be used to protect a carboxy group substituent of the compounds provided herein. Further examples of these groups are found in E. Haslam, "Protective Groups in Organic Chemistry", J. G. W. McOmie, Ed., Plenum Press, New York, N.Y., 1981, Chapter 5 and T. W. Greene, "Protective Groups in Organic Synthesis", 2nd Ed., John Wiley and Sons, New York, N.Y., 1991, Chapter 5.

The term "prodrugs" as used herein defines derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters as prodrugs are methyl, ethyl, propyl, isopropyl, n-butyl, isobutyl, tert-butyl, and morpholinoethyl.

The term "hydroxy activation agent" refers to acid halides, and acid anhydrides that are capable of converting a hydroxyl group into a leaving group labile to base treatment or nucleophilic displacement. Typical hydroxy activation agents include, but are not limited to sulfonating agents such as, methane sulfonyl chloride, p-toluenesulfonyl chloride, phenylsulfonyl chloride, trifluoromethylsulfonyl chloride, and the like, acylating agents such as isobutyl chloroformate, acetyl chloride, and the like, and halogenating reagents such as thionyl chloride, phosphorus tribromide, and the like.

The term "activated hydroxy group" refers to the moiety that results when a compound containing a hydroxy group is reacted with a hydroxy activating reagent e.g. the transformation from O—H to o-methylsulfonyl, o,p-tolunesulfonyl, o-phenylsulfonyl, o-trifluoromethylsulfonyl, o-isobutylacetyl, o-acetyl, chloro, or bromo.

"Therapeutically effective amount" means that amount of a compound that will elicit the biological or medical response of a tissue, system, or mammal that is being sought by a researcher or clinician.

"Pharmaceutically acceptable salt" refers to a salt of the compound of formula I, which is substantially non-toxic to mammals. Typical pharmaceutically acceptable salts include those salts prepared by reaction of the compounds of the present invention with a mineral or organic acid or an organic or inorganic base. Such salts are known as acid addition and base addition salts, respectively. It should be recognized that the particular counter-ion forming a part of any salt of this invention is not of a critical nature, so long as the salt as a whole is pharmaceutically acceptable and as long as the counter-ion does not contribute undesired qualities to the salt as a whole.

Acids commonly employed to form acid addition salts are inorganic acids such as, without limitation, hydrochloric acid, hydrobromic acid, hydriodic acid, sulfuric acid, phosphoric acid, and the like, and organic acids, such as, without limitation, p-toluenesulfonic acid, methanesulfonic acid, oxalic acid, p-bromophenylsulfonic acid, carbonic acid, succinic acid, citric acid, benzoic acid, acetic acid, and the like.

DETAILED DESCRIPTION OF THE INVENTION

The present invention provides novel compounds having utility as hypoglycemic and hypolipidemic agents of formula I;

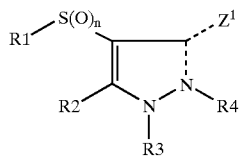

wherein:

R¹, R², R³, and R⁴ are independently alkyl, aryl, aralkyl, heteroaryl, heteroalkyl radicals of 1–20 atoms (including, but not limited to, carbon, hydrogen, oxygen, nitrogen, sulfur, phosphorus, halogen) with or without alkyl, aryl, aralkyl or heterocyclic radical substituents; $Z^1$ is independently selected from Hydrogen, oxygen, sulfur, or nitrogen; the dashed bond is a single or double bond; and n is an integer from zero to 2 or a salt or prodrug thereof.

PREFERRED COMPOUND OF THE INVENTION

Preferred for the purpose of the present invention is a compound of formula II:

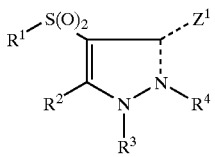

wherein:

R¹, R², R³, and R⁴ are as described above, and $Z^1$ is oxygen, sulfur, nitrogen or hydrogen connected by a single or double bond to form the carbonyl (C=O), thiocarbonyl (C=S), hydroxy (OH), thiol (SH) or amino (NH₂) functional groups.

More preferred is a compound selected from the group of compounds depicted by formula III:

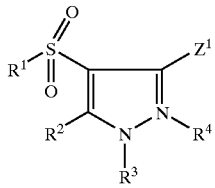

wherein:

R¹, R², $Z^1$ are as described above and R³, R⁴ are Hydrogen. Most preferred is a compound of formula IV

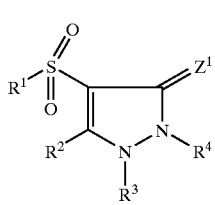

wherein;

R², R³ and R⁴ are hydrogen; and $Z^1$ is oxygen, NR⁵ or S, wherein R₅ is selected from the group consisting of H, C₁–C₄ alkyl, phenyl or benzyl.

Exemplary of preferred compounds for the present invention is a compound selected from the group consisting of:

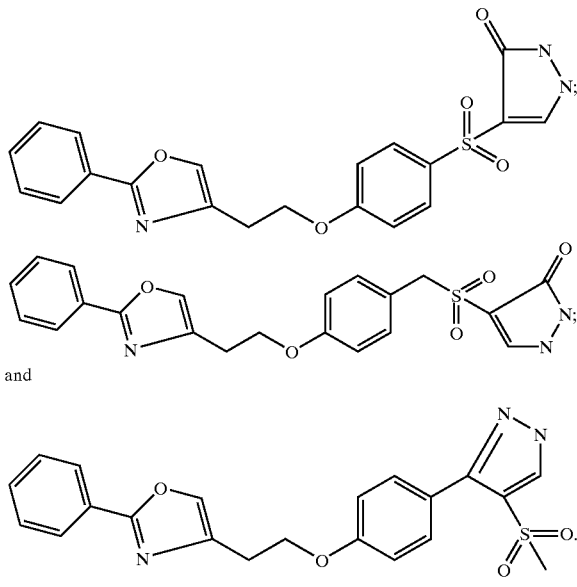

and

Pharmaceutically acceptable acid addition salts of the compounds of formula I are also aspects of this invention. Examples of such pharmaceutically acceptable salts are, without limitation, the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methoxybenzoate, phthalate, sulfonate, xylenesulfonate, phenylacetate, phenylpropionate, phenylbutyrate, citrate, lactate, -hydroxybutyrate, glycollate, tartrate, methanesulfonate, propanesulfonate, naphthalene-1-sulfonate, naphthalene-2-sulfonate, mandelate, and the like salts of the compound of formula I. The preferred acid addition salts are those formed with mineral acids, such as, without limitation, hydrochloric acid, and hydrobromic acid, and those formed with organic acids, such as, without limitation, maleic acid and methanesulfonic acid.

Exemplary of compounds of formula I useful for the purposes of this invention include:

4-(4-[2-(2-Phenyl-4-oxazolyl)ethoxy]phenylsulfonyl)-1H,2H-prazolin-3-one; 4-(4-[2-(2-Phenyl-4-oxazolyl)ethoxy]phenylmethylsulfonyl)-1H,2H-prazolin-3-one; 3-(4-(2-Phenyl-4-oxazolyl)ethoxy)phenyl-4-methylsulfonyl-1H-1,2-pyrazoline; 2-Naphthylsulfonyl-pyrazolin-3-one; and 6-(2-Fluorobenzyloxy)-2-naphthylsulfonyl-pyrazolin-3-one.

Compounds of Formula I are readily prepared by standard chemical reactions generally known to skilled practitioners and are summarized in standard texts and reference works; e.g. and i.a.: March, Advanced Organic Chemistry, Wiley-Interscience, New York 1985; Katritzky, Handbook of Heterocyclic Chemistry, Pergamon Press, London 1985, Fieser and Fieser, Reagents for Organic Synthesis, Wiley Interscience, New York, 1968–1998

Additional useful references are contained in "General methods for the acylation of sulfones", M. W. Thomasen, B. M. Handwerker, S. A. Katz, R. B. Belser, J. Org. Chem. 1988, 53, 906–907; N. N. Girotra, et.al., J. Med. Chem. 1992, 35, 3474–3482. For Example, Scheme I depicts the preparation of a typical candidate compound of the present invention by a sequence involving, first, nucleophilic displacement of an activated aromatic fluoride by an alkoxide (generated from an alcohol using a strong base such as sodium hydride and the like, in an indifferent solvent such as DMF) [March, pp 576–607], then acylation of the resulting sulfone (under the influence of a strong base such as sodium hydride and the like, in an indifferent solvent such as THF and the like) to produce a beta-sulfonyl ester. Subsequent condensation of the sulfonyl ester with a formamide acetal, such as DMA in a typical inert solvent such as THF at a moderately elevated temperature such as 50–60° C. [Fieser and Fieser, 3, 115] produces a substituted acrylate ester which cyclizes upon treatment with a diatomic nucleophile such as hydrazine to produce a heterocyclic compound such as a pyrazolin-3-one.

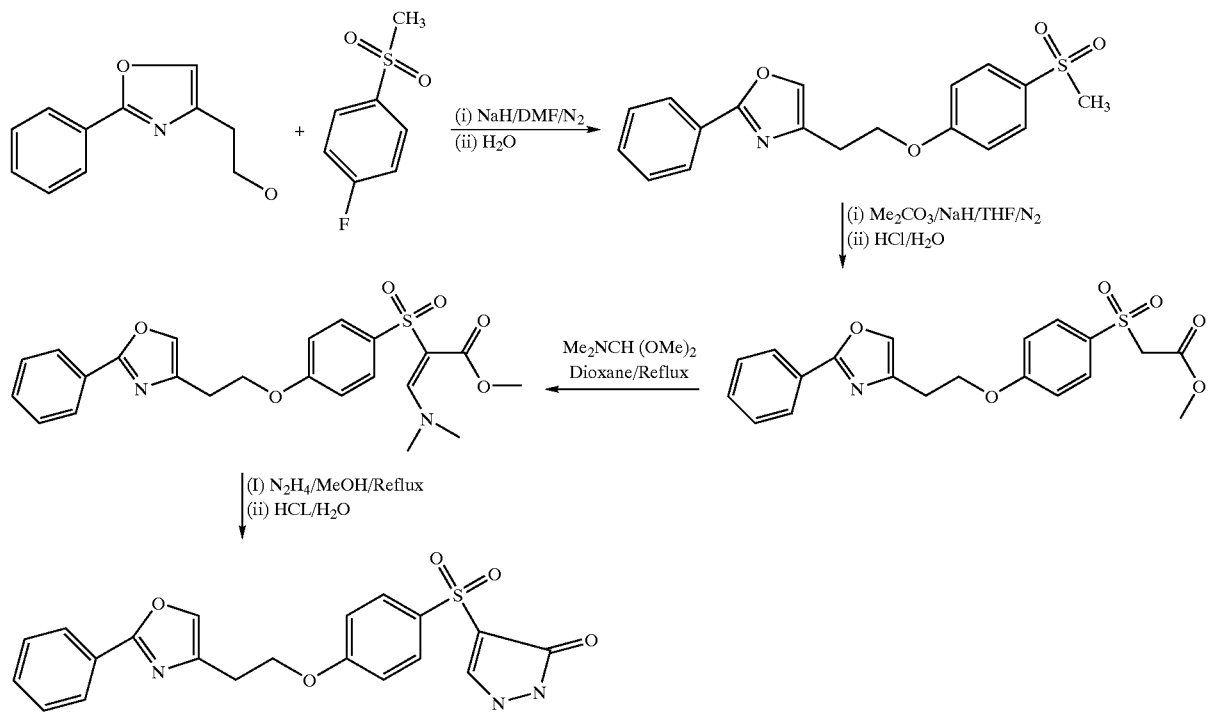

An alternate route to compounds of the present invention is depicted in Scheme 2, wherein the intermediate beta sulfonyl esters are secured by a sequence involving conversion of an alcohol to an isothiuronium salt by reaction with thiourea and a hydrohalic acid such as HBr in a convenient solvent mixture such as water/methanol, hydrolysis of the isothiuronioum halide to a thiol (which may or may not be isolated), and alkylation of the thiol with a substituted acid derivative such as methyl bromoacetate [Fieser, 1, 1165]. Subsequent oxidation of the resulting thio-oxy acid derivative with a reagent such as hydrogen peroxide affords a beta sulfonyl ester, used as described above.

Scheme 2

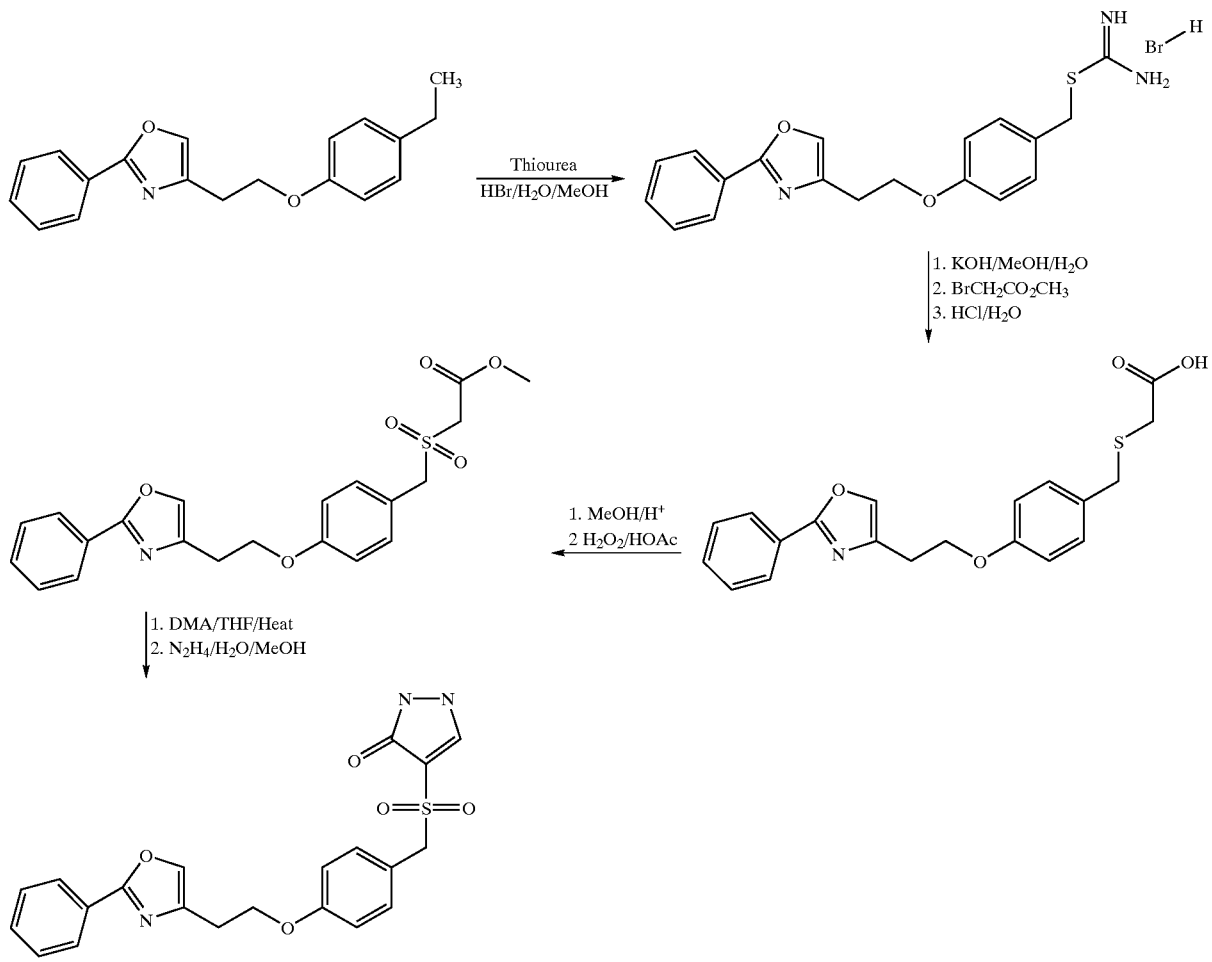

An example of the synthesis of candidate pyrazolines is depicted in Scheme 3, wherein a beta sulfonyl ketone is produced by the alkylation of an ester, such as a substituted benzoate, with an alkyl sulfone, such as dimethyl sulfone in the presence of a base such as sodium hydried in an indifferent solvent such as THF, at a convenient temperature such as 50–60° C. Condensation of the sulfonyl ketone with a reagent such as DMA produces a substituted vinyl keto sulfone, which undergoes cyclization to a heterocycle such as a pyrazoline upon treatment with a diatomic nucleophile such as hydrazine.

Scheme 3

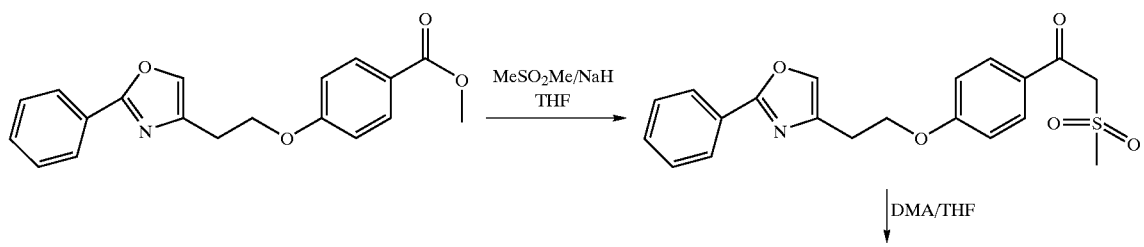

Aromatic phenols (including e.g., naphthols) may be used to produce candidate compounds of the present invention as illustrated in Scheme 4, wherein a substituted naphthol is converted to an aryl thioacetic acid derivative by means of a Newman Rearrangement [Fieser 2, 173]. Subsequent conversion to a pyrazolin-3-one then follows Scheme 2. The sequence may be carried out without purification of intermediates (cf Example 4) or by isolation and characterization of intermediates (cf Example 5).

or veterinary arts in view of a variety of factors, including without limitation, the species, age, weight, sex, and medical condition of the recipient, the severity of the condition to be treated, the route of administration, the level of metabolic and excretory function of the recipient, the dosage form employed, the particular compound and salt thereof employed, and the like.

The compounds of the present invention are preferably formulated prior to administration together with one or more

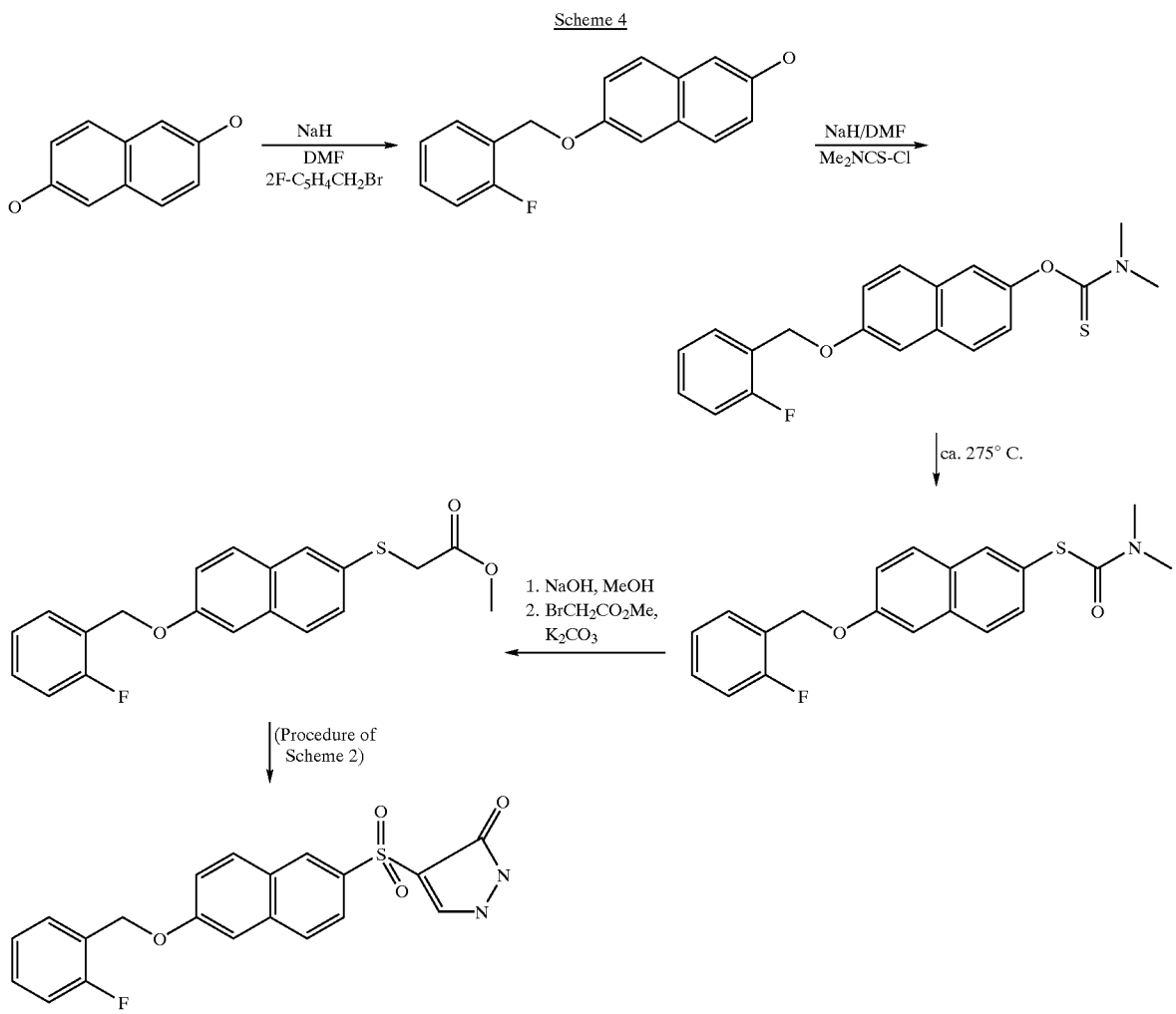

Formulation

The compounds of the present invention can be administered in oral forms, such as tablets, capsules, pills, powders, granules, elixirs, tinctures, suspensions, syrups, and emulsions. They may also be administered in parenteral forms, such as intravenous (bolus or infusion), intraperitoneal, subcutaneous, intramuscular, and the like forms, well known to those of ordinary skill in the pharmaceutical arts. The compounds of the present invention can be administered in intranasal form via topical use of suitable intranasal vehicles, or via transdermal routes, using transdermal delivery systems well-known to those of ordinary skill in that art.

A dosage regimen utilizing the compounds of the present invention is selected by one of ordinary skill in the medical pharmaceutically acceptable excipients. Excipients are inert substances such as, without limitation, carriers, diluents, flavoring agents, sweeteners, lubricants, solubilizers, suspending agents, binders, tablet disintegrating agents and encapsulating material.

Therefore, yet another embodiment of the present invention is a pharmaceutical formulation comprising a compound of the invention and one or more pharmaceutically acceptable excipients that are compatible with the other ingredients of the formulation and not deleterious to the recipient thereof. Pharmaceutical formulations of the invention are prepared by combining (e.g., mixing) a therapeutically effective amount of the compounds of the invention together with one or more pharmaceutically acceptable excipients therefor. In making the compositions of the present invention, the active ingredient may be admixed with a diluent, or enclosed within a carrier, which may be in the form of a capsule, sachet, paper, or other container. The carrier may serve as a diluent, which may be solid, semi-solid, or liquid material which acts as a vehicle, or can be in the form of tablets, pills, powders, lozenges, elixirs, suspensions, emulsions, solutions, syrups, aerosols (as a solid or in a liquid medium), ointments, containing, for example, up to 10% by weight of the active compound, soft and hard gelatin capsules, suppositories, sterile injectable solutions and sterile packaged powders.

For oral administration in the form of a tablet or capsule, the active ingredient may be combined with an oral, non-toxic, pharmaceutically acceptable carrier, such as without limitation, lactose, starch, sucrose, glucose, methyl cellulose, calcium carbonate, calcium phosphate, calcium sulfate, sodium carbonate, mannitol, sorbitol and the like; together with, optionally, disintegrating agents, such as, without limitation, maize, starch, methyl cellulose, agar, bentonite, xanthan gum, alginic acid, and the like; and optionally, binding agents, for example, without limitation, gelatin, acacia, natural sugars, beta-lactose, corn sweeteners, natural and synthetic gums, acacia, tragacanth, sodium alginate, carboxymethylcellulose, polyethylene glycol, waxes, and the like; and optionally, lubricating agents, for example, without limitation, magnesium stearate, sodium stearate, stearic acid, sodium oleate, sodium benzoate, sodium acetate, sodium chloride, talc, and the like.

In powders, the carrier is a finely divided solid which is in admixture with the finely divided active ingredient. In tablets, the active ingredient is mixed with a carrier having the necessary binding properties in suitable proportions and compacted in the shape and size desired. The powders and tablets preferably contain from about 1 to about 99 weight percent of the active ingredient which is the novel composition of the instant invention. Suitable solid carriers are magnesium carbonate, magnesium stearate, talc, sugar, lactose, pectin, dextrin, starch, gelatin, tragacanth, methylcellulose, sodium carboxymethyl cellulose, low melting waxes, and cocoa butter.

Sterile liquid formulations include suspensions, emulsions, syrups, and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

Preferably, the pharmaceutical formulation is in unit dosage form. A "unit dosage form" is a physically discrete unit containing a unit dose, suitable for administration in human subjects or other mammals. A unit dosage form can be a capsule or tablet, or a number of capsules or tablets. A "unit dose" is a predetermined quantity of the active compound of the present invention, calculated to produce the desired therapeutic effect, in association with one or more pharmaceutically acceptable excipients. The quantity of active ingredient in a unit dose may be varied or adjusted from about 0.1 to about 1000 milligrams or more according to the particular treatment involved. It may be appreciated that it may be necessary to make routine variations to the dosage depending on the age and condition of the recipient. The dosage will also depend on the route of administration.

The oral route is most preferred. Typical oral dosages of the present invention, when used for the indicated effects, will range from about 0.01 mg per kg body weight per day (mg/kg/day) to about 50 mg/kg/day, preferably from 0.1 mg/kg/day to 30 mg/kg/day, and most preferably from about 0.5 mg/kg/day to about 10 mg/kg/day. The compounds of the present invention may be administered in a single daily dose, or the total daily dose may be administered in divided doses, two, three, or more times per day. Where delivery is via transdermal forms, of course, administration is continuous.

The human to whom the compounds and formulations of the present invention are administered is afflicted with a disease or condition in which blood glucose levels are not adequately controlled without medical intervention, but wherein there is endogenous insulin present in the human's blood and or afflicted with a disease or condition wherein lipid levels are not adequately or desirably controlled as in hyperlipidemia. Non-insulin dependent diabetes mellitus (NIDDM) is a chronic disease or condition characterized by the presence of insulin in the blood, even at levels above normal, but resistance or lack of sensitivity to insulin action at the tissues. The compounds and formulations of the present invention are also useful to treat acute or transient disorders in insulin sensitivity, such as sometimes occur following surgery, trauma, myocardial infarction, and the like. The compounds and formulations of the present invention are also useful for lowering serum triglyceride levels. Elevated triglyceride level, whether caused by genetic predisposition or by a high fat diet, is a risk factor for the development of heart disease, stroke, and circulatory system disorders and diseases. The physician of ordinary skill will know how to identify humans who will benefit from administration of the compounds and formulations of the present invention.

The following formulation examples are illustrative only and are not intended to limit the scope of the invention in any way.

Formulation 1

Hard gelatin capsules are prepared by mixing the following ingredients and filling the mixture, in 460 mg quantities, into hard gelatin capsules.

| Ingredient | Quantity (mg/capsule) |
| --- | --- |
| Active ingredient | 250 |
| Starch, dried | 200 |
| Magnesium stearate | 10 |
| Total | 460 |

Formulation 2

A tablet containing 250 mg of the compound of the present invention is prepared by blending the components listed below and then compressing 665 mg of the blend into a tablet.

| Ingredient | Quantity (mg/tablet) |
| --- | --- |
| Active ingredient | 250 |
| Cellulose, microcrystalline | 400 |
| Silicon Dioxide, fumed | 10 |
| Stearic Acid | 5 |
| Total | 665 |

Formulation 3

A tablet containing 60 mg of the compound of the present invention is prepared as follows:

| Ingredient | Quantity (mg/tablet) |
| --- | --- |
| Active ingredient | 60 |
| Starch | 45 |
| Cellulose, microcrystalline | 35 |
| Polyvinylpyrrolidone, 10%, aqueous | 4 |
| Sodium carboxymethyl starch | 4.5 |
| Magnesium stearate | 0.5 |
| Talc | 1 |
| Total | 150 |

The active ingredient, starch, and cellulose are passed through a No. 45 mesh U.S. sieve and mixed thoroughly. The solution of polyvinylpyrrolidone is mixed with the resultant powders and then passed through a No. 14 mesh U.S. sieve. The granules so produced are dried at 50° C. and passed through a No. 18 mesh U.S. sieve. The sodium carboxylmethyl starch, magnesium stearate, and talc, previously passed though a No. 60 mesh U.S. sieve, are then added to the granules which, after mixing, are compressed on a tablet machine to yield tablets each weighing 150 mg.

Formulation 4

Capsules containing 80 mg of the active compound of the present invention are made as follows:

| Ingredient | Quantity (mg/capsule) |
| --- | --- |
| Active ingredient | 80 |
| Starch | 59 |
| Cellulose, microcrystalline | 59 |
| Magnesium stearate | 2 |
| Total | 200 |

The active ingredient, starch, cellulose, and magnesium stearate are blended, the blend is passed through a No. 45 mesh U.S. sieve, and then hard gelatin capsules are filled with 200 mg of the blend.

Formulation 5

Suppositories each containing 225 mg of active compound of the present invention are made as follows:

| Ingredient | Quantity (mg/suppository) |
| --- | --- |
| Active ingredient | 225 |
| Saturated fatty acid glycerides | 2,000 |
| Total | 2,225 |

The active compound is passed through a No. 60 mesh U.S. sieve and suspended in the saturated fatty acid glycerides, previously melted using the minimum heat necessary. The mixture is then poured into a suppository mold of nominal 2 g capacity and allowed to cool.

Formulation 6

Suspensions each containing 50 mg of active compound of the present invention per 5 mL dose are made as follows:

| Ingredient | Quantity per dose |
| --- | --- |
| Active ingredient | 50 mg |
| Sodium Carboxymethyl Cellulose | 50 mg |
| Syrup | 1.25 mL |
| Benzoic Acid Solution | 0.10 mL |
| Flavor | q.v. |
| Color | q.v. |
| Purified Water to total volume: | 5 mL |

The active ingredient, starch, cellulose, and magnesium stearate are blended, the blend is passed through a No. 45 mesh U.S. sieve, and then hard gelatin capsules are filled with 200 mg of the blend.

Formulation 7

An intravenous formulation may be prepared as follows:

| Ingredient | Quantity |
| --- | --- |
| Active ingredient | 100 mg |
| Sterile, isotonic saline | 1000 mL |

The compound of the present invention is dissolved in the saline and administered intravenously at a rate of 1 mL per minute to a subject in need thereof.

Formulation 8

An aerosol solution is prepared by mixing the active ingredient with ethanol and then with the propellant 22, cooled to −30° C., and transferred to a filling device. The required amount is then fed to a stainless steel container and diluted with the remainder of the propellant. The valve units are finally fitted to the container.

| Ingredient | Weight % |
| --- | --- |
| Active ingredient | 0.25 |
| Ethanol | 29.75 |
| Propellant 22 | 70.00 |
| Total | 100.00 |

Demonstration of Hypoglycemic Efficacy

Male obese-diabetic viable yellow ($A_vY$) mice were divided into two groups of 6 each. One group was fed repelletized purina 5008 Chow and the second group was fed repelletized Purina 5008 Chow, admixed with varying doses of the candidate compound. Blood samples were taken before the experiment was initiated and 7 and 14 days after initiation. Body weight and food consumption were monitored. The blood glucose level after 7 or 14 days of treatment was measured and recorded as a percent of the initial value, compared to the untreated control (first) group. The results are presented in the table 1 below; and include the dose of the candidate compound as a weight percent of the amount incorporated into the diet. Also in the table is a representative value for a positive control (a known hypoglycemic agent as disclosed by T. Sohda, K. Mizuno, Y. Momose, H. Ikeda, T. Fujita, and K. Meguro, *J. Med. Chem.*, 1992, 35, 2617) administered in the same way as a candidate compound of the present invention.

TABLE 1

| Example No. | Dose | % BG14 (BG0 = 100) |
| --- | --- | --- |
| 1 | .03 | 32 |
| 2 | .03 | 81 |
| 3 | .01 | 72 |
| 4 | .1 | 94 |
| Takeda "Compound 17" | .003 | 29.0 |

BG means blood glucose level; BG0 means blood glucose level at day zero and BG14 means blood glucose level at day 14 accordingly. Takeda "Compound 17" is disclosed by T. Sohda, K. Mizuno, Y. Momose, H. Ikeda, T. Fujita, and K. Meguro, *J. Med. Chem.*, 1992, 35, 2617.

Experimental-General

Melting points were measured using a Thomas Hoover capillary instrument and are uncorrected. Ratios are on a weight basis, except fluid mixtures for chromatography, which are on a volume basis. Temperatures are in degrees Celsius. Chromatography was performed on silica under low or medium pressure "flash" conditions as described by C. W. Still, et al., *J. Org. Chem.* 43:2923 (1978). Thin Layer Chromatography (TLC) was performed on glass plates coated with silica gel, 240 microns, grade 2.

Proton NMR spectra were obtained using at 300.15 MHz and peak positions are reported as delta values relative to an internal TMS standard.

Abbreviations g, grams
THF, Tetrahydrofuran
DMF, N,N-Dimethylformamide
DMA, N,N-Dimethylformamide Dimethyl Acetal
NaH, Sodium Hydride, a 60% (wt) dispersion in mineral oil
MsOH, Methanesulfonic Acid
mL, Milliliter
mM, Millimole
°C., Degrees Centigrade
i-PrOH, Isopropanol
MeOH, Methanol
$Et_2O$, Diethyl Ether
Mp, melting point
rt, ambient room temperature

EXAMPLES

Example 1

4-(4-[2-(2-Phenyl-4-oxazolyl)ethoxy]phenylsulfonyl)-1H,2H-prazolin-3-one (A) 4-[2-(2-Phenyl-4-oxazolyl)ethoxy]phenyl Methyl Sulfone A stirred solution of 2-(2Phenyl-4-oxazolyl)ethanol1 (12.6 g, 66 mM) in 20 mL of DMF was blanketed with nitrogen and treated with 1.95 g (48 mM) of NaH. Gas evolution began followed by the precipitation of a solid. The reaction was allowed to proceed for 5 minutes and treated with 10 g (57 mM) of 4-fluorophenylmethyl sulfone. The resulting frothy mixture was kept at 55–60° C. for 2.5 h, when TLC analysis demonstrated most of the starting materials had been consumed. The mixture was cooled, treated with ice and water and stirred. The resulting precipitate was filtered and washed with water and hexanes. Recrystallization of the solid from i-PrOH provided 10.3 g (53%) of the product as glittering flakes, mp 147–149° C.

Anal. Calcd. for $C_{18}H_{17}NO_4S$: (MW 343) C, 62.96; H, 4.99; N, 4.08. Found: C, 63.16; H, 4.91, N 4.29.

NMR(DMSO-d6): 3.05(t, 2H), 3.10 (s, 3H), 4.40(t, 2H), 7.20(d, 2H),7.55(m, 3H), 7.85(d,2H), 7.95(m, 2H), 8.05 (s, 1H)

Mass Spec. m/e 344

(B) Methyl 4-[2-(2-Phenyl-4-oxazolyl)ethoxy]phenylsulfonyl]acetate

A stirred solution of 4.5 g (13 mM) of the product from part (A) above in 50 mL of THF was treated with 10 mL (excess) of dimethyl carbonate, followed by 1.97 g (49 mM) of NaH). The initial gas evolution was allowed to subside and the mixture refluxed under nitrogen for 3 h. The cooled mixture was treated with ice, 5N HCl and extracted with ethyl acetate. The extracts were washed successively with water, 5% sodium bicarbonate, water, brine and dried over magnesium Sulfate. Removal of solvent afforded an oil which solidified on trituration with hexanes. Recrystallization from methylene chloride-Hexane provided 1.69 g (32.4%) of product as a white powder mp 112–114° C.

Anal. Cal for $C_{20}H_{19}NO_6S$ (MW 401) C, 59.84; H, 4.77; N,3.48; S, 7.99. Found. C, 59.81; H, 4.71; N, 3.66; S, 8.02.

NMR($CDCl_3$) 3.15(t, 2H),3.60 (s, 3H), 4.15 (s, 2H), 4.45(t, 2H), 7.20(d, 2H),7.55(m, 3H), 7.85(d,2H), 7.95(m, 2H), 8.05(s, 1H)]

MS. m/e 401

IR(KBr) 1750 cm−1

(C) (E/Z) Methyl 1-(4-[2-(2-Phenyl-4-oxazolyl)ethoxy]phenylsulfonyl)-2-N,N-dimethylamino Acrylate A stirred solution of 1.5 g (3.7 mM) of the compound prepared in (B) above in 20 mL of Dioxane was treated with 1.2 mL (9.0 mM) of DMA and heated to reflux 7 h. The mixture was kept at rt overnight and then concentrated in vacuo. Trituration of the residue with Et₂O produced a solid which was recrystallized from MeOH to provide 1.10 g (64%) of product as nearly white crystals, mp 111–114° C.

Anal. Cal. For C₂₃H₂₄N₂O₆S (MW 456): C, 60.51; H, 5.30; N, 6.14. Found: C, 60.58; H, 5.29; N, 6.09

NMR(CDCl₃) 2.95 (broad s, 3H), 3.15(t, 2H),3.30 (broad s, 3H), 3.60 (s, 3H), 4.45(t, 2H), 7.20(d, 2H),7.55 (m, 3H)7.55,7.85(d,2H), 7.95(m, 2H), 8.05(s, 1H)]

MS (FD+) m/e 456

IR(KBr) 1609, 1614, 1590 cm–1

(D) 4-(4-[2-(2-Phenyl-4-oxazolyl)ethoxy]phenylsulfonyl)-1H,2H-prazolin-3-one

A stirred mixture of 7.79 g (17.0 mM) of the intermediate prepared according to (C) above in 40 mL of MeOH was treated with 12 mL of 80% Hydrazine Hydrate and heated to reflux for 3 h. The resulting clear solution was partially concentrated, diluted with water and acidified to pH 2–3. The precipitate which formed overnight was collected by filtration, washed with water and recrystallized from THF/MeOH to provide 5.70 g (81%) of the product as fine white crystals mp 195–200° C. (dec.)

Anal. Cal. For C₂₀H₁₇N₃O₅S (MW 411): C, 58.39; H, 4.17; N, 10.21. Found: C, 58.58; H, 4.36; N, 10.02.

NMR (DMSO-d6) 3.05(t, 2H), 3.4 (b. s., 2H, exchanges with D2O), 4.40(t, 2H), 7.20(d, 2H), 7.55 (m, 3H), 7.85(d, 2H), 7.95(m, 2H), 8.05(s, 1H)]

Example 2

4-(4-[2-(2-Phenyl-4-oxazolyl)ethoxy]phenylmethylsulfonyl)-1H,2H-prazolin-3-one.

(A) S-4-[2-(2-Phenyl-4-oxazolyl)ethoxy]phenylmethyl Isothiuronium Bromide

A stirred mixture of 7.2 g (24 mM) of 4-[2-(Phenyl-4-oxazolyl)phenylmethanol, 2.75 g (36 mM) thiourea and 75 mL of MeOH was treated with 7 mL of 48% HBr. The resulting clear solution was heated to reflux 3 h and then kept at room temperature for 8 to 16 hours overnight. The solution was diluted with 100 mL iPrOH, concentrated to about half volume and cooled. The solid which formed was removed by filtration and washed with cold iPrOH. Recrystallization from iPrOH provided 8.62 g (81%) of product as a white solid mp 197–200° C. dec.

Anal. Cal. For C₁₉H₁₉N₃O₂S. HBr (MW 434): C, 52.54; H, 4.64; N, 9.67. Found: C, 52.38; H, 4.71; N, 9.51.

NMR: 3.05(t, 2H), 4.40(t, 2H), 4.35 (s, 2H), 7.20(d, 2H),7.55(m, 3H),7.6 (s, 1H), 7.85(d,2H), 7.95(m, 2H), 8.9–9.2(broad, 3H).

IR: 3104 (broad), 1657, 1589, 1550, 1515 cm–1

(B) Methyl S-{4-[2-(2-Phenyl-4-oxazolyl)ethoxy]phenylmethyl}sulfonylacetate

To a stirred solution of 4.5 g of 85% KOH (65.9 mM KOH) in 50 mL of MeOH was added 4.3 g (10 mM) of the intermediate prepared in part (A) above. The resulting mixture was heated to reflux under nitrogen for 4 h, during which time most of the solids had gone into solution. The cooled mixture was stirred under nitrogen for 8 to 16 hours and treated with 0.6 g of powdered KI and 2.0 mL of methyl bromoacetate. The resulting mixture was maintained under nitrogen at ambient temperature for 24 h then treated with ice and 5N HCL. The mixture was extracted with ethyl acetate and the extracts washed successively with water and brine. The extracts were dried with magnesium sulfate and the solvent removed in vacuo to provide a white powder. Trituration of the residue with Et₂O/Hexane provided 2.70 g of white crystals, mp 102–104° C. The solid was dissolved in 50 mL of MeOH, the solution treated with 0.2 mL of methanesulfonic acid and refluxed for 6 h. The bulk of the solvent was removed by distillation and the residual syrup dissolved in ethyl acetate. The ethyl acetate solution was washed successively with water, 5% sodium bicarbonate, water, brine and dried with magnesium sulfate. The solvent was removed and the residual oil stirred with 15 mL of HOAc. 4 mL of 30% hydrogen peroxide was added and the mixture stirred at ambient temperature for 8 to 16 hours. The mixture was diluted with water and extracted with ethyl acetate. The ethyl acetate extracts were washed successively with water, 5% sodium bicarbonate, water, brine and dried with magnesium sulfate. Removal of the solvent and recrystallization of the residue from methylene chloride-Hexane provided 0.92 g (22%) of product as white crystals, mp 93–95° C.

Anal. Cal. For C₂₁H₂₁NO₆S (MW 415): C, 60.71; H, 5.09; N, 3.37. Found: C, 61.01; H, 5.21; N, 3.30.

NMR: 3.05(t, 2H), 3.70 (s, 3H), 3.80 (s, 2H) 4.40(t, 2H),4.45 (s, 2H), 6.90(d, 2H), 7.30 (d, 2H), 7.55(m, 3H),7.6 (s, 1H), 7.95(m, 2H)

(C) 4-(4-[2-(2-Phenyl-4-oxazolyl)ethoxy]phenylmethylsulfonyl)-1H,2H-prazolin-3-one.

A solution of 0.90 g (2.2 mM) of the intermediate from (B) above in 20 mL of THF was treated with 0.7 mL (5 mM) of DMA and heated to reflux for 7 h. The cooled solution was evaporated in vacuo and the residual oil washed with Et₂O. A solution of the residue in 20 mL of MeOH was treated with 1 mL of 85% hydrazine hydrate and heated to reflux for 2 h. The cooled solution was treated with 100 mL 1N HCL and allowed to stand at room temperature for 8 to 16 hours and the gummy solid which had formed was filtered and washed with H₂O.

Recrystallization from iPrOH provided 0.5 g (53%) of product as a white powder, m.p. 228–230° C.

Anal. Cal. For c₂₁H₁₉N₃O₅S (MW 425): C, 59.28; H, 4.50; N, 9.88. Found: C, 59.28; H, 4.53; N 9.86.

MS m/e 425

NMR: 3.05(t, 2H), 4.40 (s, 2H) 4.38(t, 2H), 6.90(d, 2H), 7.30 (d, 2H), 7.55(m, 3H),7.6 (s, 1H), 7.95(m, 2H), (xx.x, bs, exchange with D₂O 1 h)

Example 3

3-(4-(2-Phenyl-4-oxazolyl)ethoxy)phenyl-4-methylsulfonyl-1H-1,2-pyrazoline (A) (4-(2-Phenyl-4-oxazolyl)ethoxy)phenyl Methylsulfonyl Methanone A stirred mixture of 6.23 g (19.2 mM) methyl 4-(2-phenyl-4-oxazolyl)ethoxybenzoate, 11.73 g (124 mM) dimethyl sulfone and 100 mL THF under Nitrogen was treated with 3.4 g (85 mM) of NaH). After the initial gas evolution had subsided, the mixture was heated to reflux 4 h, cooled and treated with ice. The mixture (pH ca. 12) was extracted with ethyl acetate. The EtOAc extracts were washed with H₂O, brine and dried over magnesium sulfate. Removal of solvent and trituration of the residue with hexane provided a soft white powder. Recrystallization of the residue from THF/iPrOH afforded 4.60 g (62%) of product as white flakes mp 133–135° C.

Anal. Cal. For $C_{20}H_{19}NO_5S$ (MW 385): C, 62.32; H, 4.97; N, 3.63. Found: C, 62.03; H, 4.89; N 3.67.

NMR 3.05(t, 2H), 3.10 (s, 3H) 4.40(t, 2H),4.55 (s, 2H), 7.20(d, 2H),7.55 (m, 3H), 7.85(d,2H), 7.95(m, 2H), 8.05(s, 1H)]

MS: m/e 385.

(B) E/Z 1-[4-(2-Phenyl-4-oxazolyl)ethoxy)phenyl]-1-Methylsulfonyl-2-N,N-Dimethylamino Ethene.

A stirred solution of 1.06 g (2.7 mM) of the intermediate prepared in part (A) above in 20 mL THF was treated with 1.0 mL (7.5 mM) of DMA and heated to reflux 2 h. The resulting brown solution was kept at room temperature for 8 to 16 hours, refluxed an additional 8 h and then evaporated. Trituration of the gummy residue with $Et_2O$ produced a soft white powder. Recrystallization from THF/i-PrOH afforded 1.14 g (95%) of product as white flakes m.p. 143–154° C.

Anal. Cal. For $C_{23}H_{24}N_2O_5S$ (MW 440): C, 62.71; H, 5.49; N, 6.36.

Found: C, 62.77; H, 5.59; N, 6.19.

MS: m/e 440

(C) 3-(4-(2-Phenyl-4-oxazolyl)ethoxy)phenyl-4-methylsulfonyl-1H-1,2-pyrazoline

A stirred mixture of 1.10 g (2.5 mM) of the intermediate prepared in part (B) above and 25 mL of i-PrOH was treated with 1 mL of 85% Hydrazine Hydrate and heated to reflux for 2 h, during which time the initial solid dissolved and was replaced by a new precipitate. The resulting mixture was kept at room temperature for 8 to 16 hours and diluted with water. The solid formed was removed by filtration, washed with $H_2O$ and drained. Recrystallization from THF/i-PrOH afforded 0.88 g (86%) of product as a fluffy white powder, m.p. 185–187° C.

Anal. Cal. For $C_{21}H_{19}N_3O_4S$ (MW 409): C, 61.60; H, 4.68; N, 10.26. Found: C, 61.55; H, 4.70; N, 10.14.

MS: m/e 409

NMR (DMSO-d6):2.50 (d, 6H), 3.05(t, 2H),3.10 (s, 3H), 4.40(t, 2H), 7.20(d, 2H),7.55 (m, 3H),7.66 (m, 1H), 7.85(d, 2H), 7.95(m, 2H), 8.05(s, 1H)]

(D) 3-(4-(2-Phenyl-4-oxazolyl)ethoxy)phenyl-4-methylsulfonyl-1H-1,2-pyrazoline

A stirred mixture of 0.88 g (2.0 mM) of the intermediate prepared in part (B) in 20 mL of i-PrOH was treated with 2 mL of 80% Hydrazine Hydrate and heated to reflux 6 h. After an additional 12 h at room temperature, TLC demonstrated complete consumption of the reactant. The mixture was treated with $H_2O$, heated to boiling, cooled and filtered. The white powder was washed with $H_2O$, boiled with i-PrOH, cooled and filtered. The residue was washed with Ether and dried to afford 0.55 g (67%) of product as fluffy white needles, mp. 187–189° C.

Anal. Cal. For $C_{21}H_{19}N_3O_4S$ (MW 409): C, 61.60; H, 4.68; N, 10.26. Found: C, 61.55; H, 4.70; N, 10.14.

MS: m/e 409

Example 4

(A) 2-Naphthylsulfonyl-pyrazolin-3-one

A stirred mixture of 6.2 g (24.8 mM) of 2-naphthylthioacetic acid and 40 mL of MeOH was treated with three drops of MSOH and heated to reflux for 3 h and then concentrated to ca. half volume. The cooled residue was diluted with H2O and extracted into EtOAc. The EtOAc extracts were washed with H2O, 5% sodium bicarbonate, H2O, brine and evaporated to a yellow brown oil. The residue was dissolved in 20 mL of HOAc and treated with 10 mL of 30% $H_2O_2$. The resulting solution was kept at ambient temperature for 48 h, diluted with $H_2O$ and the resulting precipitate removed by filtration. The solid was washed thoroughly with H2O and dried to produce a solid mp 73–75° C. A solution of 2.64 g (10 mM) of the solid in 30 mL of EtOAc was treated with 2 mL (excess) of DMA and heated to reflux for 3 h. The resulting dark yellow brown solution was cooled and concentrated in vacuo to provide a dark gum which solidified to tan crystals mp 126–129° C. on trituration with cold MeOH. A stirred mixture of this solid and 40 mL of MeOH was treated with 2 mL of 85% hydrazine hydrate and heated to reflux. The resulting solution was refluxed 3 h, cooled and diluted with $H_2O$. the precipitate which formed was collected by filtration, washed with $H_2O$ and dried to provide 0.92 g (33% overall) of product as fine white crystals mp 239.5° C. (dec.)

Anal. Cal. For $C_{13}H_{10}N_2O_3S$ (MW 274): C, 56.93; H, 3.68; N, 10.21. Found: C, 57.23; H, 3.90; N, 9.93.

MS: m/e 274

Example 5

6-(2-Fluorobenzyloxy)-2-naphthylsulfonyl-pyrazolin-3-one (A) 6-(2-Fluorobezyloxy)-2-naphthol A stirred solution of 15.0 g (94.0 mM) of 2,6-dihydroxynaphthalene in 60 mL of DMF was treated with 3.21 g (80.0 mM) of NaH under nitrogen. The resulting dark solution was treated dropwise with a solution of 5.94 g (31.0 mM) of 2-fluorobenzyl bromide in 20 mL of $Et_2O$ over 0.75 h. The mixture was stirred an additional 2 h then treated cautiously with 200 mL 1N HCl. The mixture was stirred 8 to 16 hours then filtered. The solid was washed thoroughly with water and dried. Flash chromatography produced a solid which was recrystallized from i-PrOH to afford 4.51 g (56%) of product as gray crystals mp 143–144° C.

Anal. Cal. For $C_{17}H_{13}FO_2$ (MW 268): C, 76.11; H, 4.88. Found: C, 75.97; H 5.00.

MS: m/e 268

NMR: 4.82(s, 1H, exchanges with $D_2O$), 2.24(s, 2H), 7.04–7.40(m, 7H), 7.50–7.71(m, 3H).

(B) N,N-Dimethyl-[6-(2-Fluorobezyloxy)-2-naphthlyoxy]-thionocarbamate

A stirred solution of 2.6 g(10 mM) of the intermediate prepared in part (A) in 20 mL of DMF was cooled in a water bath to ca. 25° C. under nitrogen and treated with 0.54 g (13.5 mM) of NaH. After gas evolution had subsided, the mixture was treated with 2.03 g (16.5 mM) of N,N-dimethyl thiocarbamyl chloride. After 3 h at ambient temperature, the mixture was treated cautiously with 250 mL of 2N HCl to produce a solid which was filtered off and washed with $H_2O$ and Hexane. Recrystallization of the solid from I-PrOH provided 2.11 g (59%) of product as tan crystals mp 165–165° C.

Anal. Cal. For $C_{20}H_{18}FNO_2S$ (MW 355): C, 67.59; H, 5.11; N, 3.94; S, 9.02. Found: C, 67.51; H, 4.99; N, 3.90; S, 8.77.

MS: m/e 355

NMR: 3.40(bs, 3H), 3.50(bs, 3H), 5.26(s, 2H), 7.00–7.90 (m, 10H).

(C) N,N-Dimethyl-[6-(2-Fluorobezyloxy)-2-naphthlythiooxy]-carbamate

A mixture of 2.3 g (6.4 mM) of the intermediate prepared in part (B) above and ca. 5 g of 2-methoxynaphthalene was heated under an air condenser under nitrogen. The resulting molten mass was heated to boiling (ca. 275° C.) for 2 h, when TLC demonstrated consumption of the staring material. The cooled mass was chromatographed over Silica with $CHCl_3$ and the product fractions combined and evaporated. Recrystallization of the dark residue from $Me_2CO$/hexane with decolorizing carbon afforded 1.0 g (48%) of product as white crystals mp 108–109° C.

Anal. Cal. For For $C_{20}H_{18}FNO_2S$ (MW 355): C, 67.59; H, 5.11; N, 3.94. Found: C, 67.73; H, 5.15; N, 3.68.

MS: m/e 355

NMR: 3.10 (bs, 6H), 5.26(s, 2H), 7.00–7.90 (m, 10H).

(D) Methyl [6-(2-Fluorobezyloxy)-2-naphthly]thioacetate

A stirred mixture of 0.9 g (2.5 mM) of the intermediate prepared in (C) and 30 mL of MeOH under nitrogen was treated with 4 ml of 2N NaOH (8 mM) and heated to reflux for 6 h. The resulting clear solution was cooled in an ice bath, treated with excess 5N HCL and the resulting mixture stirred 8–16 hours. The solid was collected by filtration, washed with $H_2O$, drained and taken up in 50 mL of $Me_2CO$/5 mL MeOH. The mixture was treated with 2.59 g (18.7 mM) of $K_2CO_3$, 0.1 g of powdered KI, 1.2 mL (12.6 mM) of methyl bromoacetate and heated to reflux for 3 h. The cooled mixture was treated with $H_2O$ and extracted with EtOAc. The EtOAc extracts were washed with $H_2O$ and brine, dried with $MgSO_4$ and evaporated. The soft slightly yellow solid residue was boiled with hexane to provide 0.6 g (66%) of the product as a soft white powder mp 88–90° C.

Anal. Cal. For C20H17FO3S (MW 356): C, 67.40; H, 4.81. Found: C, 67.27; H, 4.99.

MS: m/e356

NMR: 3.66 (s, 2H), 3.67 (s, 3H), 5.26(s, 2H), 7.00–7.90 (m, 10H).

(E) Methyl [6-(2-Fluorobezyloxy)-2-naphthlysulfonyl] acetate

A stirred mixture of 0.5 g (1.4 mM) of the intermediate prepared in (D) above in 10 mL of HOAc was treated with 5 mL (excess) of 30% $H_2O_2$ and kept at ambient temperature 24 h. the resulting clear solution was diluted with H2O and extracted with EtOAc. The extracts were washed successively with $H_2O$, bicarbonate, $H_2O$, brine, dried with MgSO4 and evaporated. The white residue was recrystallized from MeOH to provide 0.34 g (62%) of the product as slender needles mp 112–113° C.

Anal. Cal. For $C_{20}H_{17}FO_5S$ (MW 388): C, 61.85; H, 4.41; S, 8.25. Found: C, 61.60; H, 4.33; S, 8.17.

MS: m/e 388

NMR:3.70(s, 3H), 4.20(s, 2H), 5.30(s, 2H), 7.00–7.90 (m, 10H).

(F) (E/Z) Methyl 1-[6-(2-Fluorobezyloxy)-2-naphthlysulfonyl]-2-N,N-dimethylamino acrylate A solution of 0.81 g (2 mM) of the intermediate prepared as in part (E) above in 20 mL of THF was treated with 1.6 mL (9 mM) of DMA. The resulting brown solution was kept at ambient temperature under nitrogen for a total of 48 h, with an intermediate period of heating for 4 h. Evaporation of the solution provided a thick brown liquid which solidified on trituration with $Et_2O$. Recrystallization of the residue from MeOH provided 0.72 g (78%) of product as a tan powder mp 128–129° C.

Anal. Cal. For $C_{32}H_{22}FNO_5S$ (MW 443): C, 62.29; H, 5.00; N, 3.16; S, 7.23. Found: C, 62.31; H, 5.02; N, 3.09; S, 7.38.

MS m/e 444

NMR: 2.99(bs, 3H), 3.35 (bs, 3H), 3.50 (s, 3H), 5.30 (s, 2H), 7.00–7.90 (m, 10H).

(G) 6-(2-Fluoro benzyloxy)-2-naphthylsulfonyl-pyrazolin-3-one

A stirred mixture of 0.72 g (1.6 mM) of the intermediate prepared as in part(F) and 20 mL of EtOH was treated with 1.0 mL of 85% hydrazine hydrate and heated to reflux for 2 h. The resulting solution was cooled, diluted with $H_2O$ and filtered to remove a solid. The aqueous alcohol filtrate was acidified to pH 2 and extracted with EtOAc. The extracts were washed with $H_2O$, brine, dried with MgSO4 and evaporated. The residual solid was washed with small portions of cold MeOH to provide 0.15 g (23%) of the product as a white powder mp 283–285° C. (dec.)

Anal. Cal. For $C_{20}H_{15}FN_2O_4S$ (MW 398): C, 60.30; H, 3.80; N, 7.03; S, 8.05. Found: C, 60.30; H, 4.08; N, 6.92; S, 7.75.

MS: m/e 397.

What is claimed is:

1. A compound selected from the group consisting of:

4-(4-[2-(2-Phenyl-4-oxazolyl)ethoxy]phenylsulfonyl)-1H, 2H-pyrazolin-3-one; 4-(4-[2-(2-Phenyl-4-oxazolyl) ethoxy]phenylmethylsulfonyl)-1H,2H-pyrazolin-3-one; 3-(4-(2-Phenyl-4-oxazolyl)ethoxy)phenyl-4-methylsulfonyl-1H-1,2-pyrazoline; 2-Naphthylsulfonyl-pyrazolin-3-one; and 6-(2-Fluorobenzyloxy)-2-naphthylsulfonyl-pyrazolin-3-one; or a pharmaceutically acceptable salt or prodrug thereof.

2. A method of treating hyperglycemia comprising administering to a mammal in need thereof, an effective amount of a compound of claim 1.

3. A method of treating hyperlipidemia comprising administering to a mammal in need thereof, an effective amount of a compound of claim 1.

4. A pharmaceutical composition comprising a compound according to claim 1 for the treatment of a mammal afflicted with hyperlipidemia.

5. A pharmaceutical composition according to claim 1 for the treatment of a mammal afflicted with hyperglycemia.

* * * * *